US010226168B2

(12) United States Patent
Kamee et al.

(10) Patent No.: US 10,226,168 B2
(45) Date of Patent: Mar. 12, 2019

(54) MEDICAL IMAGE FORMATION APPARATUS

(71) Applicant: OLYMPUS CORPORATION, Tokyo (JP)

(72) Inventors: Hiroyuki Kamee, Koganei (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 76 days.

(21) Appl. No.: 15/221,664

(22) Filed: Jul. 28, 2016

(65) Prior Publication Data

US 2016/0331218 A1 Nov. 17, 2016

Related U.S. Application Data

(63) Continuation of application No. PCT/JP2015/051809, filed on Jan. 23, 2015.

(30) Foreign Application Priority Data

Jan. 29, 2014 (JP) .................................. 2014-014869

(51) Int. Cl.
*A61B 1/06* (2006.01)
*G03B 15/05* (2006.01)
(Continued)

(52) U.S. Cl.
CPC ........ *A61B 1/0661* (2013.01); *A61B 1/00009* (2013.01); *A61B 1/043* (2013.01);
(Continued)

(58) Field of Classification Search
CPC ....... A61B 1/45; A61B 1/0638; A61B 1/0009; A61B 1/0002; A61B 5/1459;
(Continued)

(56) References Cited

U.S. PATENT DOCUMENTS 9,523,680 B2 * 12/2016 Lim .................... G01N 33/6845
2009/0219384 A1 * 9/2009 Iketani ................. A61B 1/0638
348/45
(Continued)

FOREIGN PATENT DOCUMENTS

CN 102309307 A 1/2012
EP 2 388 626 A2 11/2011
(Continued)

OTHER PUBLICATIONS

Extended Supplementary European Search Report dated Dec. 18, 2017 in European Patent Application No. 15 74 2832.7.
(Continued)

*Primary Examiner* — Dramos Kalapodas
(74) *Attorney, Agent, or Firm* — Scully, Scott, Murphy & Presser, P.C.

(57) ABSTRACT

A medical image formation apparatus includes laser emitting elements which emit laser light rays different in wavelength, an image selection circuit to select a kind of observation image, a light source controller which controls the laser emitting elements, in accordance with an observation mode corresponding to the selected kind, an imager which images return light ray from an observation target and then outputs the return light ray as an image signal, and an image processor which forms the observation images. A first laser emitting group is controlled when the kind of selected observation image is a first observation image. A second laser emitting group is controlled when the kind of selected observation image is a second observation image. The first laser emitting group and the second laser emitting group include a first common laser emitting element.

5 Claims, 10 Drawing Sheets

(51) Int. Cl.
    *A61B 1/00*     (2006.01)
    *A61B 1/04*     (2006.01)
    *A61B 1/313*    (2006.01)
    *A61B 5/1455*   (2006.01)
    *G02B 23/24*    (2006.01)
    *G06T 5/00*     (2006.01)

(52) U.S. Cl.
    CPC .......... *A61B 1/0638* (2013.01); *A61B 1/0669* (2013.01); *A61B 1/3137* (2013.01); *A61B 5/14552* (2013.01); *G02B 23/2461* (2013.01); *G02B 23/2484* (2013.01); *G03B 15/05* (2013.01); *G06T 5/009* (2013.01); *A61B 1/063* (2013.01); *G03B 2215/0567* (2013.01); *G06T 2207/10068* (2013.01); *G06T 2207/20208* (2013.01); *G06T 2207/30101* (2013.01)

(58) Field of Classification Search
    CPC ..... A61B 1/0661; A61B 1/043; A61B 1/0669; A61B 1/063; A61B 5/14556; A61B 1/0051; G02B 23/2484; G02B 23/2461; G03B 15/05; G03B 2215/0567; G06T 2207/30101; G06T 2207/10068
    See application file for complete search history.

(56) References Cited

U.S. PATENT DOCUMENTS

| | | | |
|---|---|---|---|
| 2012/0010465 A1* | 1/2012 | Erikawa | A61B 1/05 600/109 |
| 2012/0245410 A1 | 9/2012 | Saito | |
| 2013/0245410 A1* | 9/2013 | Saito | A61B 1/00009 600/339 |

FOREIGN PATENT DOCUMENTS

| | | | |
|---|---|---|---|
| EP | 2 526 854 A1 | 11/2012 | |
| EP | 2 638 843 A1 | 9/2013 | |
| JP | 2009-207584 A | 9/2009 | |
| JP | 2011-200572 A | 10/2011 | |
| JP | 2011200572 A * | 10/2011 | ........... A61B 1/0638 |
| JP | 2012-016545 A | 1/2012 | |
| JP | 2013-027432 A | 2/2013 | |
| JP | 2013027432 A * | 2/2013 | ............... A61B 1/06 |
| JP | 2013-188365 A | 9/2013 | |

OTHER PUBLICATIONS

International Search Report dated Apr. 14, 2015 issued in PCT/JP2015/051809.
Neumann, A. et al., "Four-color laser white illuminant demonstrating high color-rendering quality", Optics Express (Jul. 4, 2011), vol. 19, No. S4, pp. A982-A990.
English translation of International Preliminary Report on Patentability dated Aug. 11, 2016 together with the Written Opinion received in related International Application No. PCT/JP2015/051809.
Japanese Office Action dated Sep. 5, 2017 in Japanese Patent Application No. 2014-014869.
Chinese Office Action dated Jun. 21, 2017 in Chinese Patent Application No. 201580006447.2.
Japanese Office Action dated Jun. 5, 2018 in Japanese Patent Application No. 2014-014869.

* cited by examiner

| | 1/4 frame | 2/4 frame | 3/4 frame | 4/4 frame |
|---|---|---|---|---|
| Lighting lasers | Lasers 1 and 2 | Lasers 3, 4, and 5 | Lasers 6 and 7 | Lasers 2, 4, 5, and 6 |
| Application | Special light 1 | Special light 2 | Special light 3 | White light image |

MEDICAL IMAGE FORMATION APPARATUS

CROSS-REFERENCE TO RELATED APPLICATIONS

This application is a Continuation Application of PCT Application No. PCT/JP2015/051809, filed Jan. 23, 2015 and based upon and claiming the benefit of priority from the prior Japanese Patent Application No. 2014-014869, filed Jan. 29, 2014, the entire contents of both of which are incorporated herein by reference.

BACKGROUND OF THE INVENTION

1. Field of the Invention

The present invention relates to a medical image formation apparatus.

2. Description of the Related Art

In contrast to conventionally used gas light sources, solid-state light sources have such advantages as low power consumption, high connection efficiency, small sizes, high-speed switchability. Technical innovations for such solid-state light sources are remarkable. Among these solid-state light sources, a solid-state laser in particular has such a feature as extremely high optical density in an emission area. Owing to this feature, what is known as fiber light sources configured by combining the solid-state laser with, for example, optical fibers are under active development. The fiber light sources are suited to illumination in a thin structure, and are being further applied to, for example, endoscopes.

As an example of a medical image formation apparatus that uses the fiber light source, Jpn. Pat. Appln. KOKAI Publication No. 2011-200572, for example, provides an electronic endoscope system capable of simultaneously acquiring and simultaneously displaying one or two kinds of images selected by, for example, a user from a microscopic vessel image, an oxygen saturation image, and a blood vessel depth image in addition to a white light image. In Jpn. Pat. Appln. KOKAI Publication No. 2011-200572, multiple solid-state light sources for broadband light ray, multiple lasers for the microscopic vessel image, multiple lasers for the oxygen saturation image, and multiple lasers for the blood vessel depth image are provided as light sources. In Jpn. Pat. Appln. KOKAI Publication No. 2011-200572, multiple images are acquired by simultaneously or sequentially applying multiple light sources corresponding to a selected image to a target.

BRIEF SUMMARY OF THE INVENTION

A medical image formation apparatus according to an aspect of the invention comprises: laser emitting elements which emit laser light rays different in wavelength; an image selection circuit to select a kind of observation image; a light source controller which controls lighting of the laser emitting elements, in accordance with an observation mode corresponding to a combination of the selected kind of observation image; an imager which images return light ray of the laser light ray from an observation target and then outputs the return light ray as an image signal; and an image processor which forms the observation images from the image signal from the imager, wherein lightning of a first laser emitting group which includes anyone of the laser emitting elements is controlled by the light source controller when the kind of selected observation image is a first observation image, lightning of a second laser emitting group which includes any one of the laser emitting elements is controlled by the light source controller when the kind of selected observation image is a second observation image, and the first laser emitting group and the second laser emitting group include a first common laser emitting element.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described with reference to the drawings. First, a prerequisite technique for the present embodiments is described. It has heretofore been considered that the emission of light having no wavelength lack in the whole visible light is essential to a white illumination apparatus which is high in quality and high in image reproduction accuracy. However, it has recently been increasingly obvious that even illumination light ray which is a combination of single-wavelength light rays such as laser light rays is high enough in the performance (color rendering properties) as illumination light ray (e.g., see A. Neumann et al., Opt. Exp., 19, S4, A982 (Jul. 4, 2011)).

Figure 1:
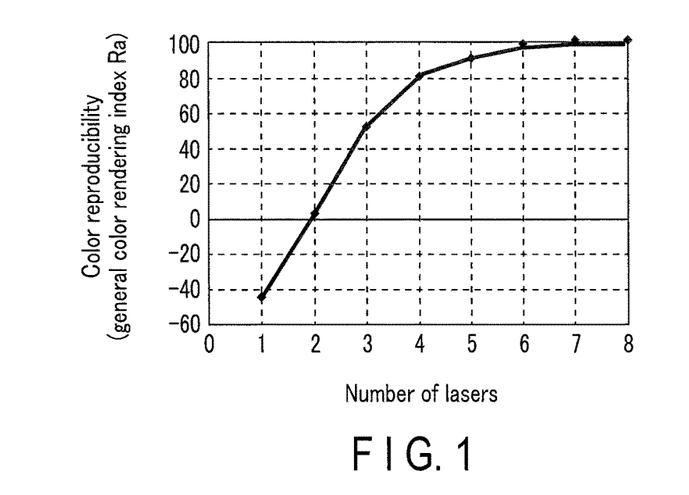
FIG. 1 is a graph showing results of the calculation of a general color rendering index Ra for various wavelengths and various numbers of lasers.

The applicant calculated a general color rendering index Ra which is one of an illuminator quality evaluation parameter defined by, for example, Japanese Industrial Standards (JIS), for various wavelengths and various numbers of lasers. As a result, as shown in FIG. 1, it was found that performance equal to or more than that of conventionally used general illumination having a broad spectrum could be obtained by an appropriate combination of laser light rays of different wavelengths. Specifically, at least four lasers allow the general color rendering index Ra to be 80, and allow sufficient performance as an illumination light source to be obtained.

A laser can output light ray higher in light density and parallelism from a smaller emission area than a gas light source or an LED. Therefore, a laser as a white light observation light source that requires color rendering properties has an advantage of being easy to highly efficiently introduce into a small-diameter light ray guiding component such as a fiber in an observation apparatus such as an endoscope apparatus' assuming observations in closed spaces (low power consumption, high-luminance illumination). Owing to a narrow spectral characteristic of the laser, it is also possible to obtain the advantage of ease of accurately acquiring the wavelength characteristic of a target part for a particular substance for special light observations that have been extensively developed in the field of endoscopes in recent years. The special light observations include, for example, observations of a blood vessel enhanced image, an oxygen saturation image, and an autofluorescence image. Each of the observation images is described below.

1, Blood Vessel Enhanced Image

Figure 2A:
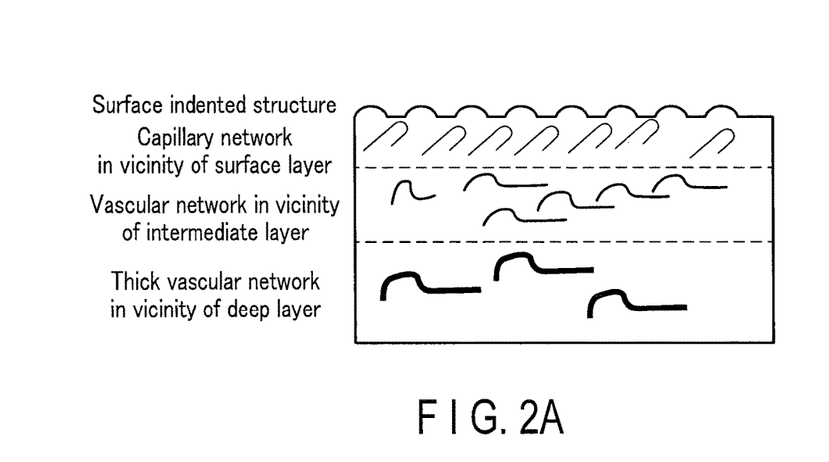
FIG. 2A is a diagram schematically showing a sectional structure of a living mucous membrane.
Figure 2B:
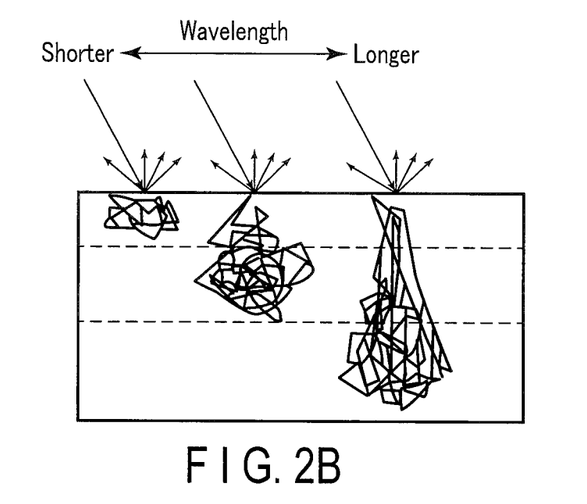
FIG. 2B is a diagram schematically showing the relation between the wavelengths and penetration depths.

It is known that when light rays ranging from ultraviolet light ray to near-infrared light ray are applied to the inside of a living body, the application of the light ray having a longer wavelength leads to a greater light penetration depth due to the scattering characteristic and absorption characteristic of the living body. For example, if a living mucous membrane has a sectional structure that is schematically shown in FIG. 2A, the light ray which has entered the living body penetrates the living body nearly to the penetration depth, and is, for example, absorbed and scattered in the range of this depth and then returns. If this return light ray is observed, information regarding the periphery of a deep area of the penetration depth can be observed. As shown in FIG. 2B, a wavelength light ray (B light) having a short wavelength (400s nm) only penetrates to the vicinity of the surface layer, and is absorbed and scattered in the vicinity of this part. The return light ray in this instance is emitted from the surface of the living body. As shown in FIG. 2B, a wavelength light ray (G light) having an intermediate wavelength (500s nm) penetrates to a range deeper than the surface layer, and is absorbed and scattered in the vicinity of this part. The return light ray in this instance is emitted from the surface of the living body. Owing to this return light ray, information regarding a deeper part can be acquired in comparison to that in the case of the wavelength light ray having the short wavelength. Moreover, as shown in FIG. 2B, a wavelength light ray (R light) having a long wavelength (600s nm) penetrates to a much deeper range, and is absorbed and scattered in the vicinity of this part. The return light ray in this instance is emitted from the surface of the living body. Owing to this return light ray, information regarding a deeper part can be acquired in comparison to that in the case of the wavelength light ray having the intermediate wavelength.

Figure 3:
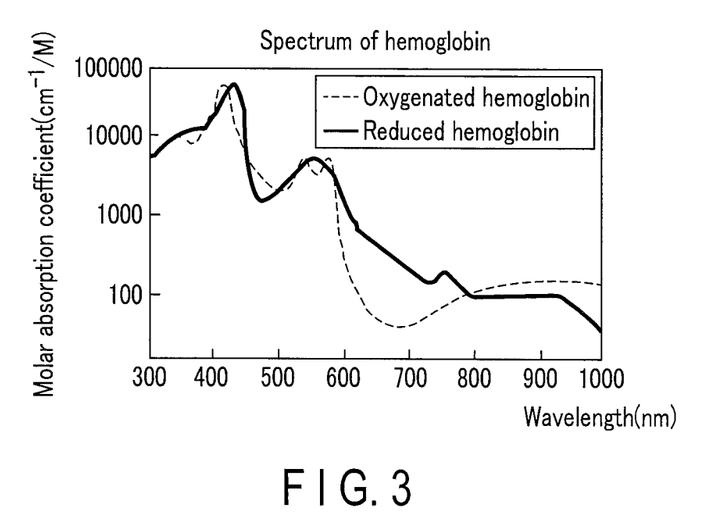
FIG. 3 is a graph showing the wavelength dependence of the absorption coefficient of blood hemoglobin.

FIG. 3 shows the wavelength dependence of the absorption coefficient of blood hemoglobin. As shown in FIG. 3, there is a slight difference of absorption spectrum between oxygenated hemoglobin and reduced hemoglobin. When light ray having a wavelength of 400s nm at which the absorption coefficient of hemoglobin is high is applied to the living body, an image in which blood vessels existing in the surface layer of the living body are mainly enhanced can be acquired. Similarly, when light ray having a wavelength of 500s nm at which the absorption coefficient of hemoglobin is high is applied to the living body, an image in which blood vessels existing in the intermediate layer of the living body are mainly enhanced can be acquired. When light ray having a wavelength of 600 nm or more is applied to the living body, an image in which blood vessels existing in the deep layer are mainly enhanced can be acquired. These observation images are blood vessel enhanced images.

2, Oxygen Saturation Image

The oxygen saturation of hemoglobin is calculated by obtaining the amount of oxygenated hemoglobin in the total amount of hemoglobin. As is evident from FIG. 3, wavelengths of 450 nm, 540 nm, and 805 nm are wavelengths at which there is little difference of absorption coefficient between oxygenated hemoglobin and reduced hemoglobin. In contrast, wavelengths of 430 nm, 560 nm, and 760 nm are wavelengths at which the reduced hemoglobin is higher in absorption coefficient, and wavelengths of 470 nm, 590 nm, and 840 nm are wavelengths at which the oxygenated hemoglobin is higher in absorption coefficient. Thus, light ray having a wavelength at which the absorption coefficients of the oxygenated hemoglobin and the reduced hemoglobin are reversed is selected and applied to the living body, and image information in each wavelength range obtained in this way is allocated to, for example, each of red, green, and blue colors and observed, so that changes of the oxygen saturation can be more easily taken as the changes of the color of the image. Such observation images are oxygen saturation images. Here, the penetration depth of light ray is greater at longer wavelengths as described above, so that an oxygen saturation image regarding blood vessels in the surface layer can be displayed when light ray having a wavelength of 400s nm is used, an oxygen saturation image regarding blood vessels in the intermediate layer can be displayed when light ray having a wavelength of 500s nm is used, and an oxygen saturation image regarding blood vessels in the deep layer can be displayed when light ray having a wavelength of 600 nm or more is used.

3, Autofluorescence Image

Figure 4A:
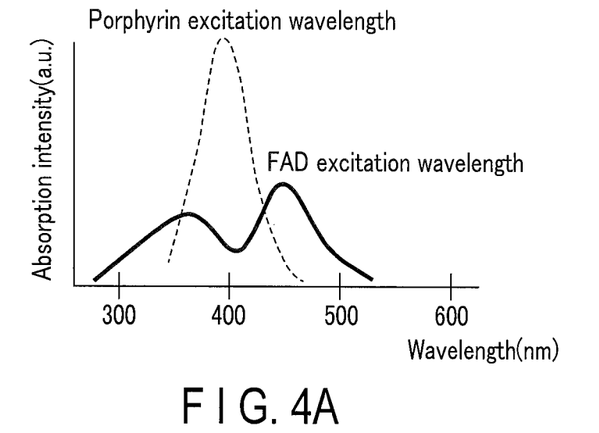
FIG. 4A is a graph showing absorption intensity characteristics regarding autofluorescent substances.
Figure 4B:
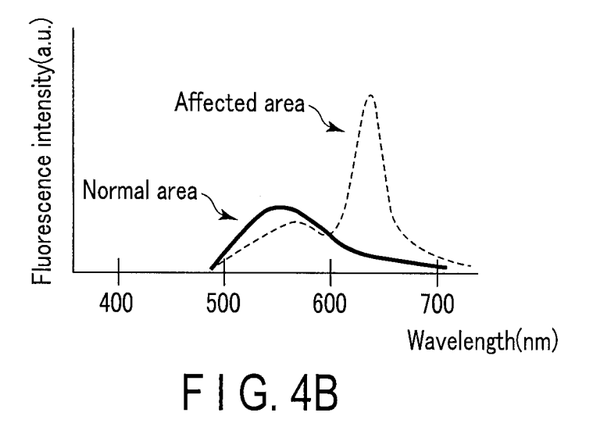
FIG. 4B is a graph showing fluorescence intensity characteristics.

FIG. 4A is a graph showing absorption intensity characteristics regarding autofluorescent substances. FIG. 4B is a graph showing fluorescence intensity characteristics. These graphs show the absorption intensity characteristics and fluorescence intensity characteristics of Flavin Adenine Dinucleotide (FAD) and porphyrin which are autofluorescent substances correlated with tumors. As is evident from the graph in FIG. 4A, porphyrin generates fluorescence by light ray having a central wavelength of 400 nm, and FAD generates fluorescence by light ray having a central wavelength of 380 nm and light ray having a central wavelength of 450 nm. Images obtained by imaging such fluorescences are autofluorescence images. Here, the fluorescence intensity of autofluorescence varies between an affected area and a normal area. That is, while fluorescence having a peak at around 550 nm is generated in the normal area, fluorescence having two peaks at 560 nm and 630 nm is generated in the affected area. It is known that porphyrin is accumulated in an area affected by, for example, cancer. Therefore, fluorescence of 630 nm regarding the affected area shown in FIG. 4B is fluorescence derived from porphyrin. Thus, by capturing the difference of fluorescence intensity of porphyrin, it is possible to distinguish the affected area from the normal area (reference: Tamura, Mamoru, "Series/Photobiology Vol. 6 Photomedicine Diagnosis", edited by Photobiology Association of Japan, Kyoritsu Shuppan Co., Ltd., Mar. 18, 2001).

[First Embodiment]

Figure 5:
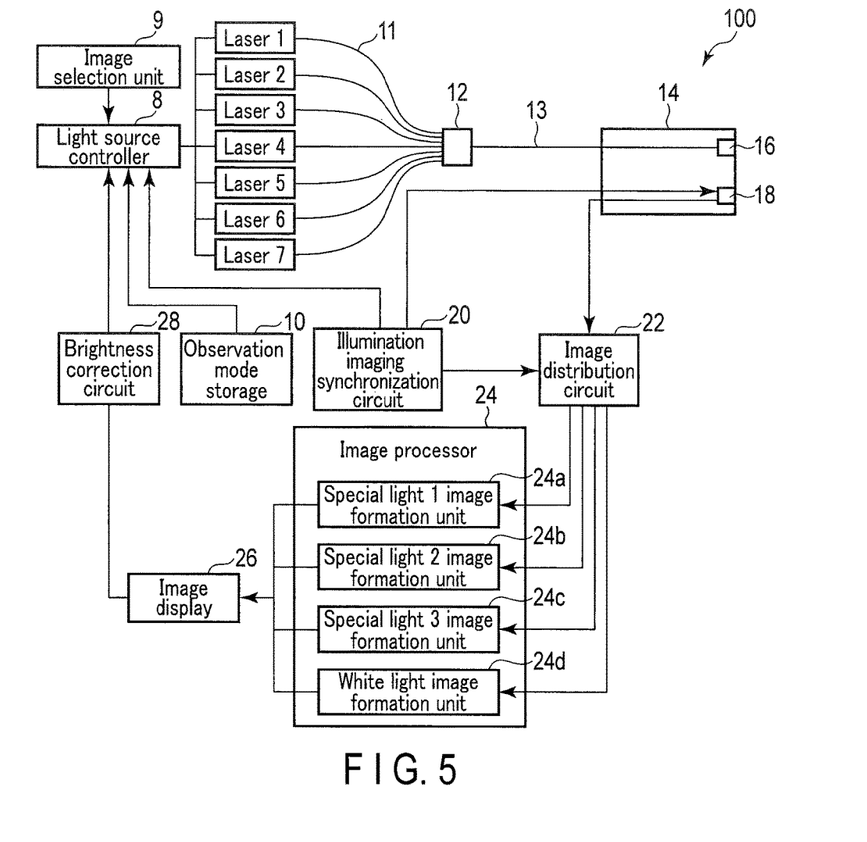
FIG. 5 is a block diagram showing the configuration of a medical image formation apparatus according to a first embodiment of the present invention.

FIG. 5 is a block diagram showing the configuration of a medical image formation apparatus according to a first embodiment of the present invention. This medical image formation apparatus 100 displays a special light image 1, a special light image 2, a special light image 3, and a white light image with high image accuracy. The special light images are observation images which are obtained by the application of light ray having a particular wavelength and in which a particular feature of an observation target is enhanced. The special light image 1 as an example is an autofluorescence image. The special light image 2 as an example is a blood vessel enhanced image. Moreover, the special light image 3 as an example is an oxygen saturation image. The white light image is a normal observation image which is obtained by the application of white light ray and in which the particular feature of the observation target is not enhanced. This white light image is used in, for example, screening.

The medical image formation apparatus 100 shown in FIG. 5 includes laser emitting elements (hereinafter briefly referred to as lasers) 1 to 7 as illumination light sources. These lasers are, for example, semiconductor lasers, and are different in emission wavelength. By way of example, the laser 1 applies light ray having a wavelength of 400 nm, the laser 2 applies light ray having a wavelength of 450 nm, the laser 3 applies light ray having a wavelength of 420 nm, the laser 4 applies light ray having a wavelength of 540 nm, the laser 5 applies light ray having a wavelength of 640 nm, the laser 6 applies light ray having a wavelength of 590 nm, and the laser 7 applies light ray having a wavelength of 560 nm.

The lasers 1 to 7 are connected to a light source controller 8 (a light source control unit). The light source controller 8 is connected to an image selection unit 9 (an image selection circuit) and an observation mode storage 10 (an observation mode storage unit). The image selection unit 9 is an operational component such as a touch panel, and receives an operation by a user to select a kind of observation image. The observation mode storage 10 stores a laser output condition (e.g., laser lighting start timing, a lighting period, and a lighting cycle) for each observation mode suited to a combination of the observation images selected by the image selection unit 9. The light source controller 8 acquires the laser output condition corresponding to an observation mode from the observation mode storage 10, and controls the lighting of the lasers 1 to 7 so that the observation images selected by the image selection unit 9 can be formed under the acquired laser output condition. Details will be described later.

Figure 6:
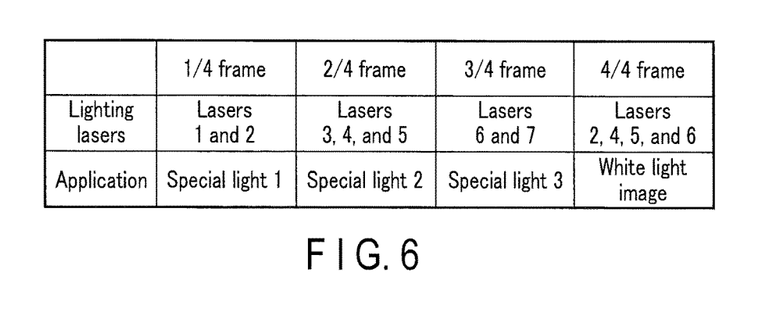
FIG. 6 is a diagram showing an example of a laser output condition in which all of a special light image 1, a special light image 2, a special light image 3, and a white light image are selected.

For example, an example of a laser output condition in which all of the special light image 1 (autofluorescence image), the special light image 2 (blood vessel, enhanced image), the special light image 3 (oxygen saturation image), and the white light image are selected is shown in FIG. 6. This laser output condition is a laser output condition for an observation mode in which the selected four observation images are simultaneously displayed. When a cycle in which an image is displayed is one frame, a 1/4 frame is a period to form the special light image 1 in the example of FIG. 6, and the lasers 1 and 2 are turned on in this period. A 2/4 frame is a period to form the special light image 2, and the lasers 3, 4, and 5 are turned on in this period. A 3/4 frame is a period to form the special light image 3, and the lasers 6 and 7 are turned on in this period. A 4/4 frame is a period to form the white light image, and the lasers 2, 4, 5, and 6 are turned on in this period. In the present embodiment, the lasers used to form the special light images are also used to form the white light image. Therefore, the number of lasers has only to be 7.

The lasers 1 to 7 are connected to a combiner 12 via optical fibers 11. The combiner 12 multiplexes laser light rays guided by the optical fibers 11. The combiner 12 is connected to a light distribution conversion member 16 provided at the distal end of a scope insertion portion 14 via an optical fiber 13. The light distribution conversion member 16 adjusts the distribution of a mixed light ray guided by the optical fiber 13 to a state suited to imaging (e.g. an optimum light distribution spread angle), and then emits the light ray toward the unshown observation target. Here, the light distribution conversion member 16 is preferably, for example, a lens, a surface diffusion component having a light diffusion function in the surface, an internal diffusion component including therein one of micro components different in refractive index and reflectance, or a multiple optical component which is a combination of the above.

An imager 18 (an imaging unit) is further provided at the distal end of a scope insertion portion 14. The imager 18 has, for example, red (R), green (G), and blue (B) image pickup devices (e.g. CCD image pickup devices) so that the image pickup devices of each color are regularly arranged flush. The R image pickup devices are image pickup devices having a peak of sensitivity in an R wavelength band (about 600 nm). Similarly, the G image pickup devices are image pickup devices having a peak of sensitivity in a G wavelength band (about 540 nm). The B image pickup devices are image pickup devices having a peak of sensitivity in a B wavelength band (about 480 nm). Each of these image pickup devices photoelectrically converts the light ray having the corresponding wavelength band to generate an image signal for each color.

An illumination imaging synchronization circuit 20 (an illumination imaging synchronization unit) is connected to the imager 18. The illumination imaging synchronization circuit 20 is also connected to the light source controller 8 and an image distribution circuit 22 (an image distribution unit). The illumination imaging synchronization circuit 20 outputs synchronization signals to the light source controller 8, the imager 18, and the image distribution circuit 22 to synchronize the illuminations by the lasers 1 to 7, imaging by the imager 18, and image distribution by the image distribution circuit 22.

The imager 18 is connected to the image distribution circuit 22. The image distribution circuit 22 is connected to each of image formation units (image information circuits) provided in an image processor 24, that is, a special light 1 image formation unit 24a, a special light 2 image formation unit 24b, a special light 3 image formation unit 24c, and a white light image formation unit 24d. The image distribution circuit 22 sends, to the image formation units, an image signal received from the imager 18 in response to the input of the synchronization signal from the illumination imaging synchronization circuit 20. The special light 1 image formation unit 24a forms the special light image 1 (autofluorescence image) from the received image signal. The special light 2 image formation unit 24b forms the special light image 2 (blood vessel enhanced image) from the received image signal. The special light 3 image formation unit 24c forms the special light image 3 (oxygen saturation image) from the received image signal. The white light image formation unit 24d forms the white light image from the received image signal.

An image display 26 (an image display unit) receives the observation images formed by the image formation units of the image processor 24, and displays the observation images so that, for example, the user can easily recognize the observation images. For example, the image display 26 divides one screen into four parts to display the respective observation images in parallel.

A brightness correction circuit 28 (a brightness correction unit) receives the observation images from the image display 26, and then determines the brightness of the observation images displayed on the image display 26. When the brightness of the observation images displayed on the image display 26 is not proper brightness, the brightness correction circuit 28 outputs a correction signal to the light source controller 8 so that the brightness of the observation images will be the proper brightness.

Figure 7:
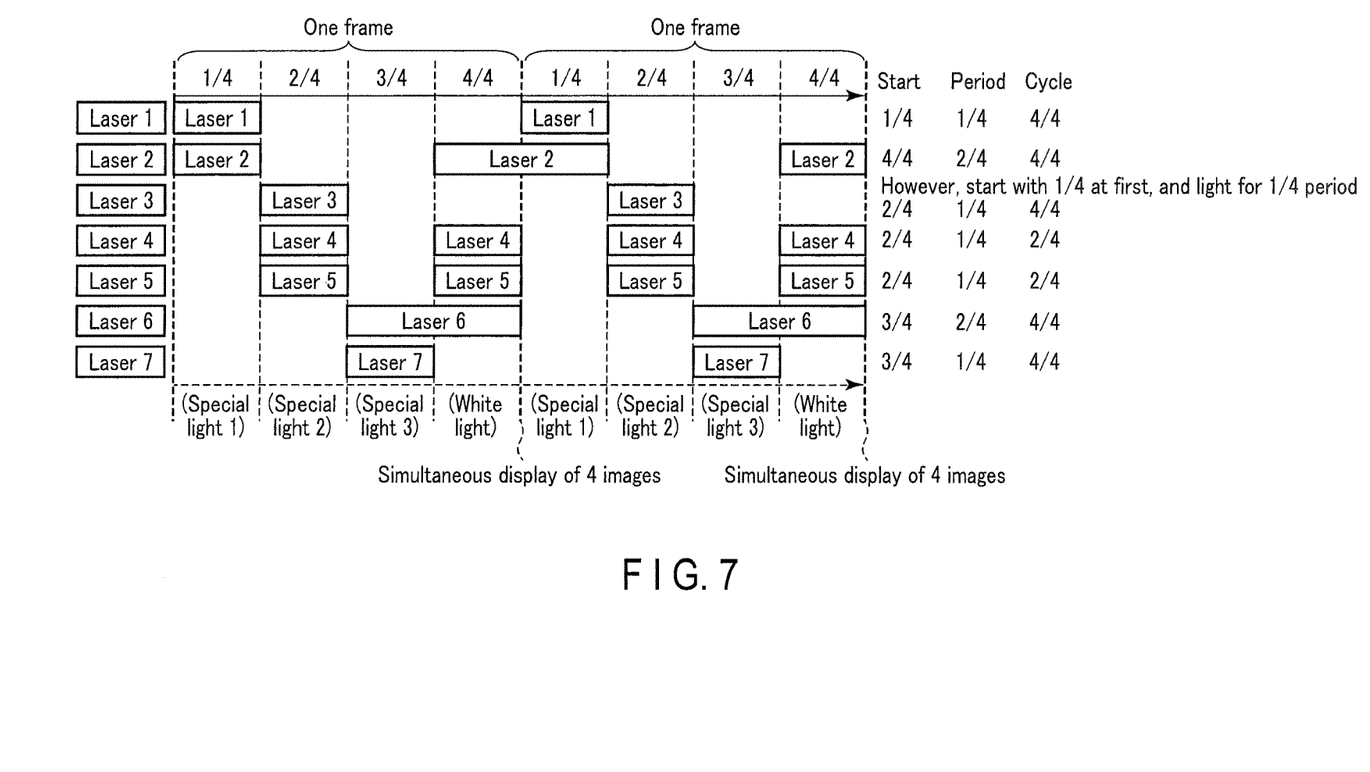
FIG. 7 is a diagram showing an example of a laser output condition in which the special light images 1, 2, and 3, and the white light image are simultaneously displayed.

Next, the operation of the medical image formation apparatus 100 according to the present embodiment is described. First, the user operates the image selection unit 9 to select an observation image. By way of example, all of the special light images 1, 2, and 3 and the white light image are selected. When an observation image is selected, the light source controller 8 acquires, from the observation mode storage 10, a laser output condition corresponding to the observation mode suited to the selected observation image. FIG. 7 shows an example of a laser output condition in which the special light images 1, 2, and 3, and the white light image are simultaneously displayed. As shown in FIG. 7, the laser 1 is only used to form the special light image 1 (autofluorescence image). Therefore, the lighting start timing of the laser 1 is the start timing of a 1/4 frame which is the formation period of the special light image 1. The lighting period of the laser 1 is the period of 1/4 of one frame. Moreover, the lighting cycle is the period of one frame. In contrast, the laser 2 is used to form the special light image 1 and to form the white light image. Therefore, the lighting start timing of the laser 2 is the start timing of the 1/4 frame which is the formation period of the special light image 1 and the start timing of the 4/4 frame which is the formation period of the white light image. However, when repeated display is performed, the 4/4 frame and the 1/4 frame are continuous as shown in FIG. 7. Therefore, the actual lighting start timing of the laser 2 is the start timing of the 1/4 frame and the start timing of the 4/4 frame only in the initial frame, and is the start timing of the 4/4 frame in the previous frame in and after the second frame. The lighting period of the laser 2 is the period of 1/4 of one frame only in the initial 4/4 frame, and is the period of 1/2 of one frame in the subsequent frames. Moreover, the lighting cycle of the laser 2 is the period of 3/4 of one frame only in the initial 1/4 frame to the 4/4 frame, and is the period of one frame in the subsequent frames. The laser 3 is only used to form the special light image 2 (blood vessel enhanced image). Therefore, the lighting start timing of the laser 3 is the start timing of a 2/4 frame which is the formation period of the special light image 2. The lighting period of the laser 3 is the period of 1/4 of one frame. Moreover, the lighting cycle is the period of one frame. The laser 4 is used to form the special light image 2 and to form the white light image. Therefore, the lighting start timing of the laser 4 is the start timing of the 2/4 frame which is the formation period of the special light image 2 and the start timing of the 4/4 frame which is the formation period of the white light image. The lighting period of the laser 4 is the period of 1/4 of one frame. Moreover, the lighting cycle is the period of a 1/2 frame. The laser 5 is used to form the special light image 2 and to form the white light image. Therefore, the lighting start timing of the laser 5 is the start timing of the 2/4 frame which is the formation period of the special light image 2 and the start timing of the 4/4 frame which is the formation period of the white light image. The lighting period of the laser 5 is the period of 1/4 of one frame. Moreover, the lighting cycle is the period of a 1/2 frame. The laser 6 is used to form the special light image 3 (oxygen saturation image) and to form the white light image. Therefore, the lighting start timing of the laser 6 is the start timing of the 3/4 frame which is the formation period of the special light image 3 and the start timing of the 4/4 frame which is the formation period of the white light image. The 3/4 frame and the 4/4 frame are continuous, so that the actual start timing of the laser 6 is the start timing of the 3/4 frame. The lighting period of the laser 6 is the period of 1/2 of one frame. Moreover, the lighting cycle is the period of one frame. The laser 7 is only used to form the special light image 3. Therefore, the lighting start timing of the laser 7 is the start timing of a 3/4 frame which is the formation period of the special light image 3. The lighting period of the laser 7 is the period of 1/4 of one frame. Moreover, the lighting cycle is the period of one frame.

In accordance with the above output condition and the synchronization signal from the illumination imaging synchronization circuit 20, the light source controller 8 turns on the lasers 1 to 7. The light source controller 8 includes electronic circuits configured to process signals such as the synchronization signal. The imager 18 images return light rays, from the observation target, of the laser light rays emitted from the lasers 1 to 7 in accordance with the synchronization signal from the illumination imaging synchronization circuit 20 to generate an image signal, the sends the generated image signal to the image distribution circuit 22.

Figure 8:
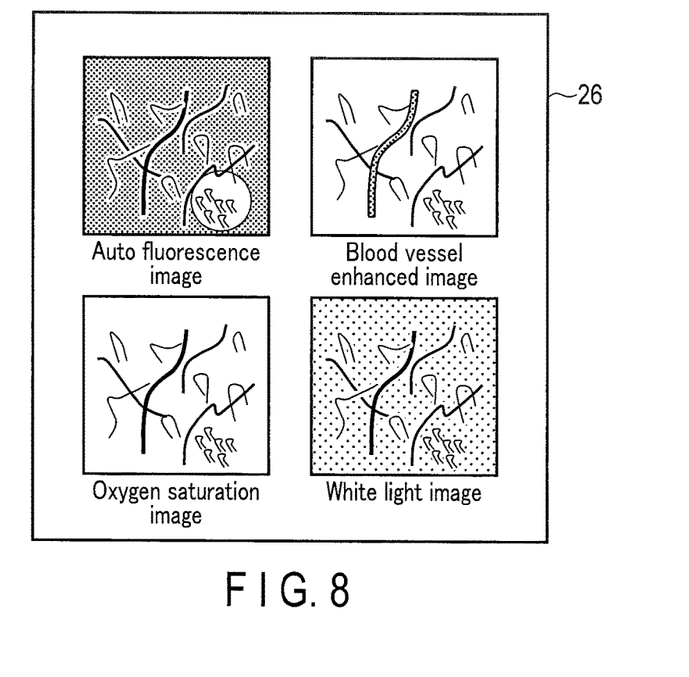
FIG. 8 is a diagram showing an example of parallel display of four observation images.

The image distribution circuit 22 identifies the kind of observation image to be formed by the synchronization signal from the illumination imaging synchronization circuit 20, and in accordance with the result of this identification, sends the image signal received from the imager 18 to the necessary image formation units among the special light 1 image formation unit 24a, the special light 2 image formation unit 24b, the special light 3 image formation unit 24c, and the white light image formation unit 24d. The image formation units form corresponding observation images from the received image signal, and send the formed observation images to the image display 26. The image display 26 displays the received observation images so that the user can easily see the observation images. For example, the image display 26 displays four observation images in parallel as shown in FIG. 8.

The observation images formed in the image formation unit are input to the brightness correction circuit 28 from the image display 26. The brightness correction circuit 28 instructs the light source controller 8 to correct the outputs of the lasers 1 to 7 so that the brightness of the observation images to be displayed on the image display 26 will be proper.

Figure 9:
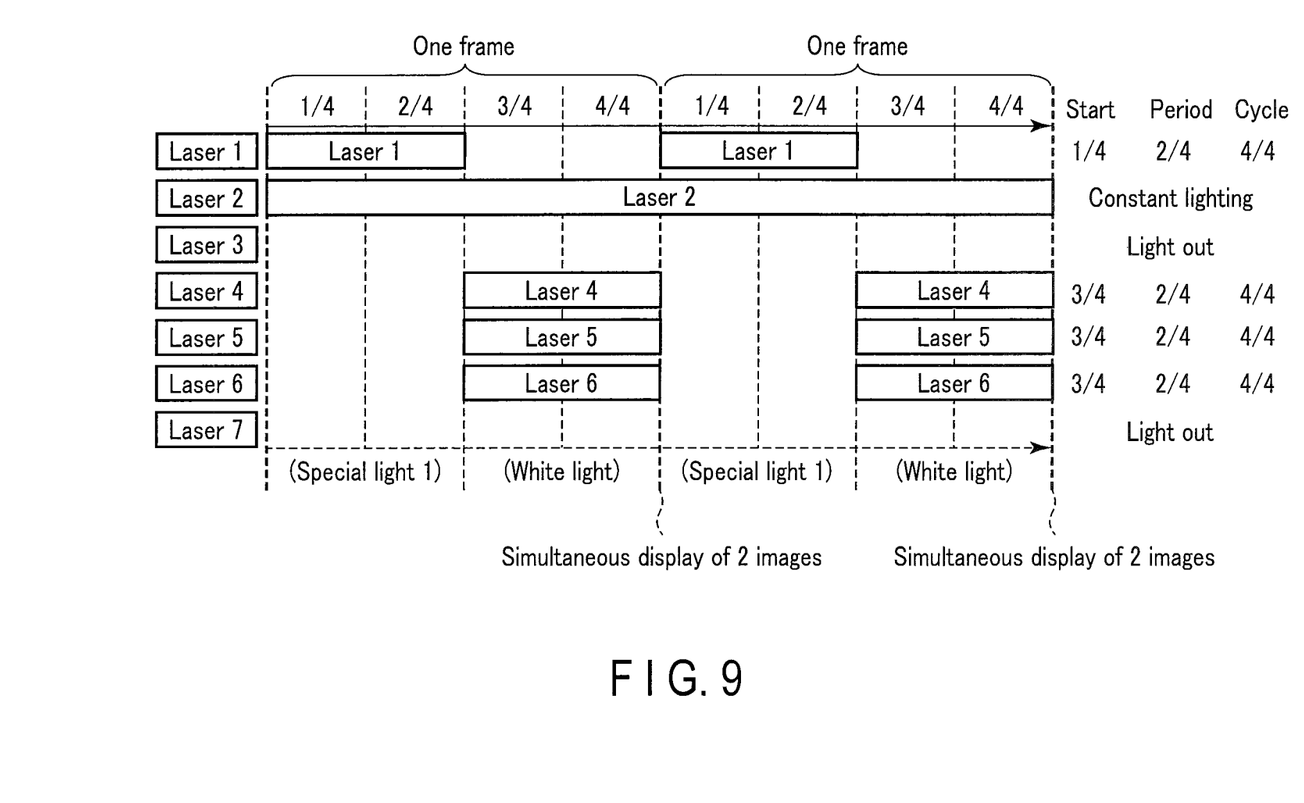
FIG. 9 is a diagram showing an example of a laser output condition in which the special light image 1 and the white light image are only selected.
Figure 10:
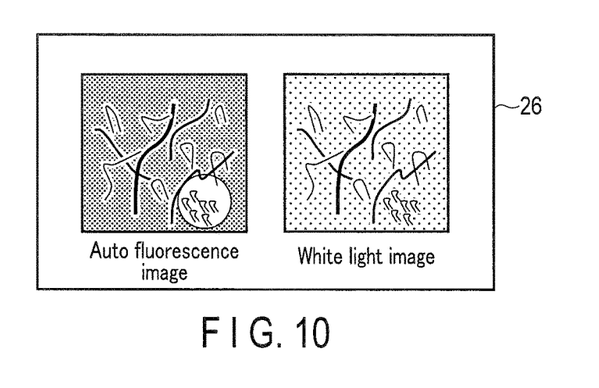
FIG. 10 is a diagram showing an example of parallel display of two observation images.

FIG. 9 shows an example of a laser output condition in which the special light image 1 and the white light image are only selected. When two observation images are only selected, the two observation images are displayed in parallel as shown in FIG. 10. In such an observation mode, two observation images have only to be formed in one frame. Therefore, as shown in FIG. 9, the lighting periods of the lasers 1, 4, 5, and 6 have only to be the period of ½ of one frame. The laser 2 may be kept turned on. In the example of FIG. 9, the formation period of the observation image can be longer, so that if the period of one frame is the same as that in the example of FIG. 7, the application time of the laser light to the observation target and the imaging period can be longer than those in the example of FIG. 7. Therefore, brighter observation images can be displayed in the example of FIG. 9 than in the example of FIG. 7.

As described above, in the present embodiment, the lasers are used to form the white light ray and the special light rays. The lasers can be highly efficiently introduced into a small-diameter light ray guiding component such as a fiber with ease, and can provide considerably bright illumination light in comparison to an LED light source or a gas light source. The laser is used to form the special light ray so that image information specific to its wavelength can be acquired, in comparison to a light source having a broad spectrum such as the LED light source. Therefore, the image accuracy is high.

Furthermore, some of the lasers for the special light rays are utilized to construct the white light image, so that the number of lasers can be reduced for reduction in costs and volume. Since four lasers for the white light image are prepared, the color rendering properties of the white light image are ensured. Moreover, other lasers are not turned on when the white light image is acquired, so that the white light image with high image accuracy can be formed. Since more than one kind of special light image are also used in common, the number of lasers can be further reduced for reduction in costs and volume.

An image desired by the user can be only formed by the image selection unit 9. Thus, there is no unnecessary lighting of the lasers, and there are no unnecessary image acquisition periods. Therefore, the lighting period of the laser and the imaging period for one observation image are maximized in one frame. Consequently, an image with high image accuracy can be acquired.

There is no unnecessary driving of the lasers if the laser lighting start timings, the laser lighting periods, and the laser lighting cycles corresponding to the observation modes are stored in the observation mode storage 10. This can also reduce power consumption. If the lighting cycles of different lasers are independently changed, the laser can be kept turned on across the frames in which different kinds of images are obtained. Thus, a common laser can be lit without any circuit load. This can also reduce power consumption.

An image signal is transferred to the image formation unit 60 by the illumination imaging synchronization circuit 20 by proper timing. This can also reduce power consumption.

Here, the medical image formation apparatus 100 according to the present embodiment is, but not exclusively, configured to create the white light image only by the lasers prepared for the special light images. In the case of a configuration that cannot create a high-quality white light image only by the lasers prepared for the special light images, a laser for the white light image may be additionally prepared. Although a different laser is prepared for each of more than one kind of laser light ray used for the special light ray in the medical image formation apparatus 100 according to the present embodiment, the same laser may also be used if there is any available technique. For example, the excitation central wavelength of porphyrin and the wavelength at which the reducing substance spectrum corresponds to that of an oxide regarding hemoglobin are the same wavelength of 450 nm. Therefore, one laser of 450 nm alone may be used for the laser to form the autofluorescence image and the laser to form the oxygen saturation image.

[Second Embodiment]

Figure 11:
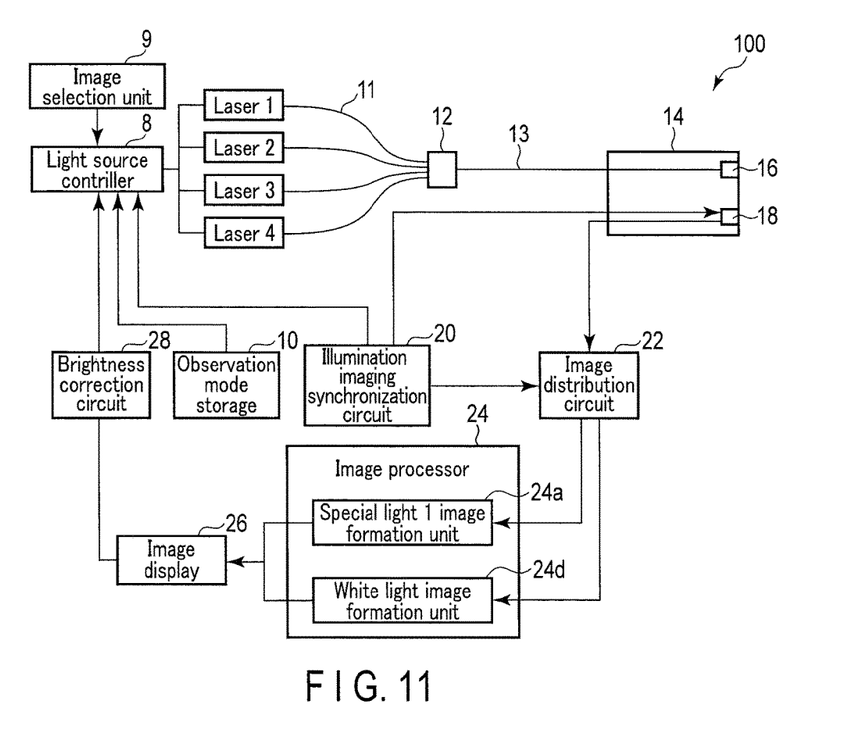
FIG. 11 is a block diagram showing the configuration of a medical image formation apparatus according to a second embodiment of the present invention.

Next, a second embodiment of the present invention is described. FIG. 11 is a block diagram showing the configuration of a medical image formation apparatus according to the second embodiment of the present invention. The medical image formation apparatus 100 according to the present embodiment is simpler in configuration than that in the first embodiment. The same components as those in the first embodiment are not described below.

The medical image formation apparatus 100 according to the second embodiment has lasers 1 to 4 as illumination light sources. By way of example, the laser 1 applies light ray having a wavelength of 400 nm, the laser 2 applies light ray having a wavelength of 450 nm, the laser 3 applies light having a wavelength of 540 nm, and the laser 4 applies light ray having a wavelength of 640 nm. In the second embodiment, two observation images: a special light image 1 (blood vessel enhanced image) and a white light image are only formed at the maximum. Therefore, there are also two image formation units alone.

Figure 12:
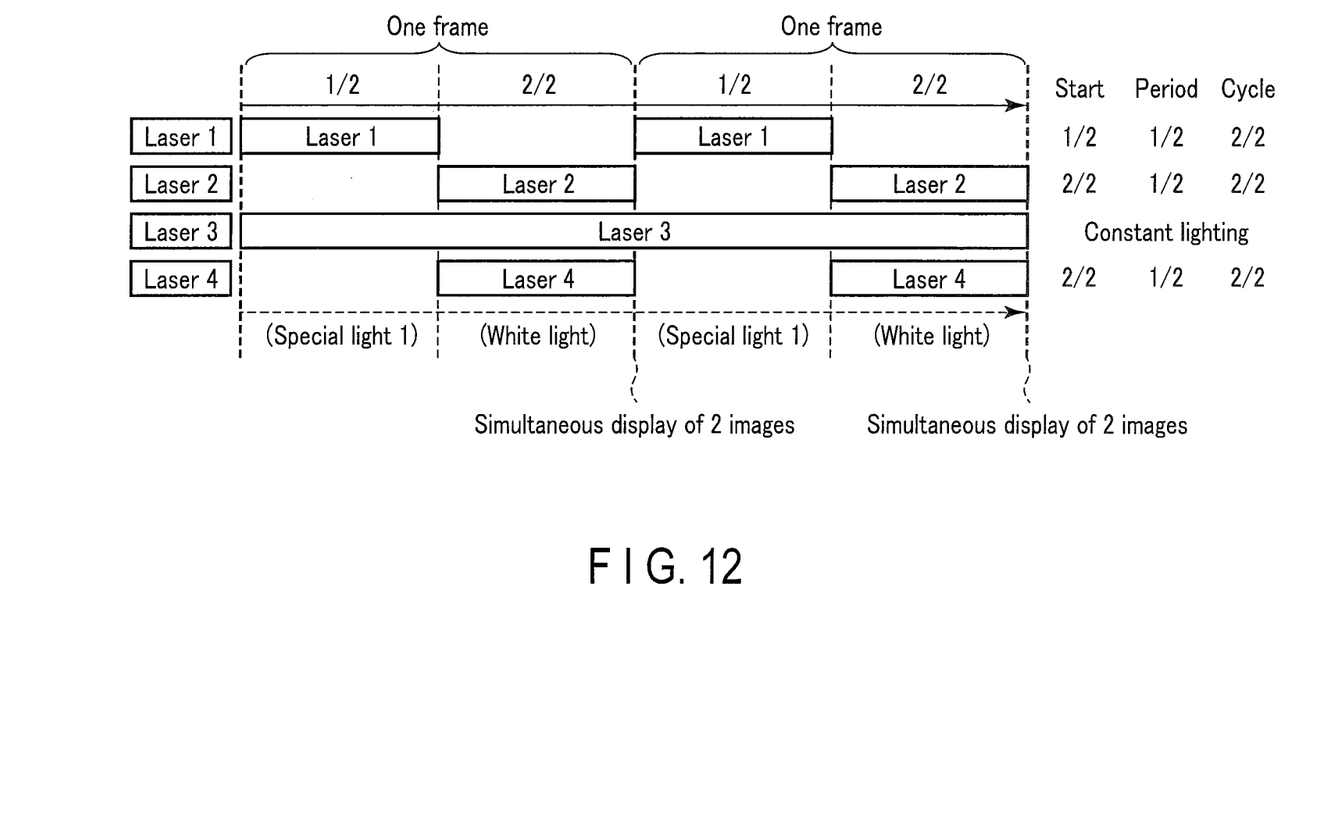
FIG. 12 is a diagram showing an example of a laser output condition in which both of the special light image 1 and the white light image are selected in the second embodiment of the present invention.
Figure 13:
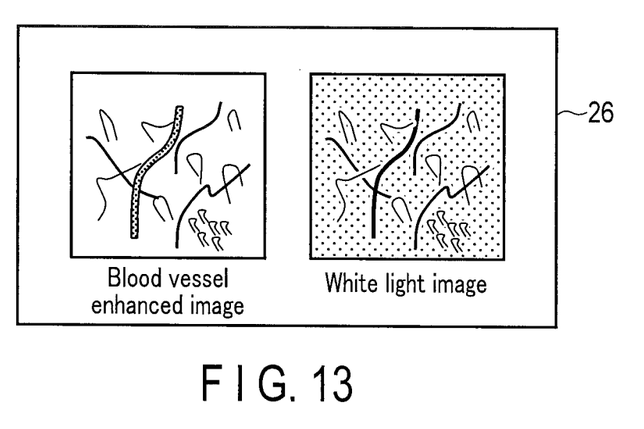
FIG. 13 is a diagram showing an example of parallel display of two observation images in the second embodiment of the present invention.

FIG. 12 shows an example of a laser output condition in which the special light image 1 and the white light image are only selected in the second embodiment. As shown in FIG. 12, the laser 1 and the laser 3 are turned on in the formation period of the special light image 1. The laser 2, the laser 3, and the laser 4 are turned on in the formation period of the white light image. The lighting periods and laser lighting cycles may be similar to those in FIG. 9. In this second embodiment, two observation images shown in FIG. 13 are displayed in parallel.

As described above, according to the present embodiment, the number of lasers and the number of other components can be much smaller than those in the first embodiment. The individual functions can be simpler than in the first embodiment, so that lower costs, a lower volume, and low power consumption can be achieved than in the first embodiment. The observation modes that are truly necessary for the user can be only formed, so that the laser lighting period and imaging period for one observation image are maximized in one frame. Consequently, an image with high image accuracy can be acquired.

The laser is newly provided for the white light image in the second embodiment, so that it is possible to obtain a white light image having high color rendering properties even if the number of lasers is three.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image formation apparatus comprising:
a light source comprising a plurality of lasers, wherein each of the plurality of lasers is configured to emit a laser light having a different wavelength;
an image selection circuit configured to receive a selection from a user of a combination of kinds of observation images to be displayed in one frame, wherein the kinds of observation images comprise:
a white light image;
a first special light image; and
a second special light image; and
a light source controller configured to control the light source to light individual groups of lasers in a corresponding one of a plurality of irradiation periods to irradiate an observation target, wherein each of the individual groups of lasers correspond to one of the kinds of observation images in the combination of kinds of observation images selected by the user;
an image sensor configured to photoelectrically convert return light from the observation target irradiated by the laser light from the individual groups of lasers lit by the light source control, to image signals; and
an image processor configured to:
generate the combination of kinds of observation images based on the image signals; and
control a display to display the combination of kind of observation images selected by the user in the one frame,
wherein the light source controller is configured to;
in response to the white light image being selected as part of the combination of kinds of observation images, control the light source to light a white light image group of the plurality of lasers in one period of the plurality of irradiation periods;
in response to the first special light image being selected as part of the combination of kinds of observation images, control the light source to light a first special light image group of the plurality of lasers in a second period of the plurality of irradiation periods; and
in response to the second special light image being selected as part of the combination of kinds of observation image, control the light source to light a second special light image group of the plurality of lasers in a third period of the plurality of irradiation periods,
wherein the white light image group of the plurality of lasers and the first special light image group of the plurality of lasers comprise a first common laser that is lit in the one period and the second period of the plurality of irradiation periods, and wherein the white light image group of the plurality of lasers and the second special light image group of the plurality of lasers comprise a second common laser that is lit in the one period and the third period of the plurality of irradiation periods.

2. The medical image formation apparatus according to claim 1, wherein the light source controller is configured to control the light source to light the white light image group, the first special light image group and the second special light image group of the plurality of lasers based on lighting start timings, lighting periods, and lighting cycles of each of the plurality of lasers, stored in a storage.

3. The medical image formation apparatus according to claim 1, wherein the light source controller is configured to light at least four lasers as a group to irradiate the observation target, wherein the at least four lasers are selected such that the image signals that are converted by the image sensor from the return light from the observation target irradiated by the laser light from the at least four lasers are processed by the image processor to generate the white light image.

4. The medical image formation apparatus according to claim 1 wherein the number of lasers included in the white light image group is larger than the number of lasers included in the first special light image group.

5. The medical image formation apparatus according to claim 1, further comprising an illumination imaging synchronization circuit configured to output signals for synchronously controlling the image sensor and the light source controller.

* * * * *